United States Patent [19]

Jacobs et al.

[11] Patent Number: 4,745,104
[45] Date of Patent: May 17, 1988

[54] PSEUDOPTEROSIN AND SYNTHETIC DERIVATIVES THEREOF

[75] Inventors: Robert S. Jacobs, Santa Barbara; William H. Fenical, Del Mar, both of Calif.

[73] Assignee: The Regents of the University of California, Berkeley, Calif.

[21] Appl. No.: 723,214

[22] Filed: Apr. 15, 1985

[51] Int. Cl.$^4$ .................. A61K 31/70; C07H 15/24
[52] U.S. Cl. ............................. 514/33; 536/18.1
[58] Field of Search .................... 536/18.1; 514/33

[56] References Cited

U.S. PATENT DOCUMENTS 4,521,592  6/1985  Dahment et al. ................ 536/4.1

Primary Examiner—J. R. Brown
Assistant Examiner—Elli Peselev
Attorney, Agent, or Firm—Poms, Smith, Lande & Rose

[57] ABSTRACT

Methods for treating mammals to reduce pain, reduce cell proliferation and/or reduce inflammation are described based on administering to the mammals compounds having the formula

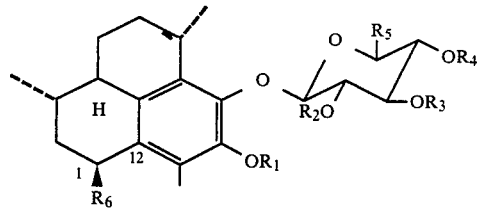

wherein $R_1$, $R_2$, $R_3$ and $R_4$ are hydrogen or an acyl residue hydrocarbon having from 1 to 6 carbon atoms, $R_5$ is hydrogen or $CH_2OH$ and $R_6$ is a functionalized hydrocarbon having from 1 to 10 carbon atoms. Natural and synthetic 1,12-seco derivatives of pseudopterosin with similar utilities are disclosed. Synthetic compositions having the above general formula which are useful in the method are disclosed.

22 Claims, No Drawings

PSEUDOPTEROSIN AND SYNTHETIC DERIVATIVES THEREOF

This invention was made with Government support under Grant No: 80-AA-D-00120 with the National Oceanic & Atmospheric Administration to the University of California. The Government has certain rights in this invention.

BACKGROUND OF THE INVENTION

The present invention relates generally to compounds having anti-inflammatory, anti-proliferative and analgesic activity and methods for using these compounds to reduce inflammation, cell proliferation and pain in mammals. More specifically, the present invention relates to natural and synthetic tricarbocyclic diterpene glycosides and their seco analogs which have been found to have anti-inflammatory, anti-proliferative and analgesic activity when administered to mammals.

Caribbean gorgonians (O. Gorgonacea, Ph. Cnidaria) are a diverse group of marine mammals which are commonly known as sea feathers, sea whips and sea fans. A wide variety of Caribbean gorgonians are found in abundance in the shallow-water reefs of the West Indian region. A few of the Caribbean gorgonians have been analyzed for their chemical content and found to be a source of many diverse organic substances such as steroids, prostaglandins, lactones, sesquiterpenoid derivatives and diterpenoid metabolites. Some of these substances have been found to be biologically active.

Since only a small percentage of the total number of Caribbean gorgonian species have been examined for natural chemical products, there has been a continuing effort by a number of researchers to examine additional gorgonian species in order to isolate possible novel natural chemical compounds.

Recently, a number of selected Caribbean gorgonians were studied in depth to isolate and identify natural chemical products (Look, S. A., Studies of the Natural Products Chemistry of Selected Caribbean Gorgonians, Ph.D. Dissertation, University of California, 1983). The contents of the dissertation published in connection with this study are hereby incorporated by reference. Numerous novel chemicals were isolated and identified during this study. One of the novel natural chemical compounds isolated during the study was pseudopterosin. Pseudopterosin is a tricarbocyclic diterpene glycoside having the chemical structure

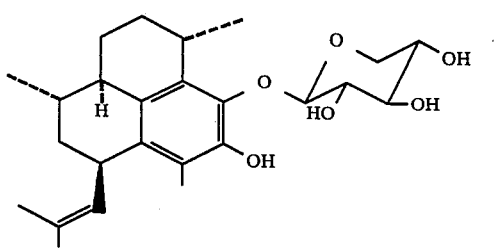

SUMMARY OF THE INVENTION

The present invention is based on the discovery that pseudopterosin and certain natural and synthetic derivatives of pseudopterosin, along with their seco-analogs, are effective as: anti-inflammatory agents; anti-proliferative agents; and analgesic agents.

One feature of the present invention involves a method for treating mammals suffering from pain to reduce pain which comprises administering to the mammal a pain reducing effective amount of a composition consisting essentially of a compound having the generalized structure

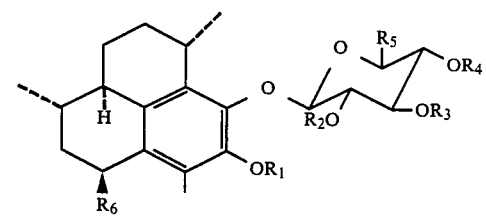

wherein $R_1$, $R_2$, $R_3$ and $R_4$ are hydrogen or an acyl function (—COR) having from 1 to 6 carbon atoms, $R_5$ is hydrogen or $CH_2OH$, and $R_6$ is a hydrocarbon having from 1 to 10 carbon atoms; and a pharmaceutically acceptable carrier compound therefor.

Another feature of the present invention involves a method for treating mammals to reduce inflammation comprising the step of administering a compound as set forth in the preceding paragraph to the mammal in an inflammation reducing effective amount. A further feature involves the use of the compounds defined in the preceding paragraph in a method for treating mammals to reduce the proliferation of proliferating cells.

The present invention also includes a new group of synthetic compounds which are useful in the above methods and which are synthetic derivatives of pseudopterosin. These synthetic compounds have the generalized structure

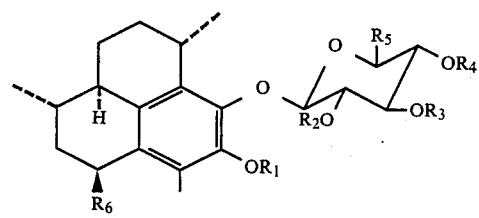

wherein $R_1$, $R_2$, $R_3$ and $R_4$ are hydrogen or an acyl residue (—COR) having from 1 to 6 carbon atoms; $R_5$ is hydrogen or $CH_2OH$; $R_6$ is a hydrocarbon having from 1 to 10 carbon atoms; and wherein if $R_6$ is 2-methyl-1-propene, then $R_5$ is $CH_2OH$ or if $R_6$ is 2-methyl-1-propene and $R_5$ is hydrogen, then three or less of said $R_1$, $R_2$, $R_3$ or $R_4$ are hydrogen and if one of $R_1$, $R_2$, $R_3$ and $R_4$ is acetate, then two or less of said $R_1$, $R_2$, $R_3$ and $R_4$ are hydrogen.

The present invention also includes pharmaceutical compositions for use as an anti-inflammatory agents, anti-proliferative agents and/or analgesic agents which consist essentially of an effective amount of one or more of the above defined synthetic compounds and a pharmaceutically acceptable carrier.

The above discussed and many other features and attendant advantages of the present invention will become apparent as the invention becomes better understood by reference to the following detailed description.

DETAILED DESCRIPTION OF THE INVENTION

The compounds of the present invention fall into three basic groups: (1) naturally occurring pseudopterosin and the naturally occurring derivatives of pseudopterosin which have been isolated from Caribbean gorgonians of the genus Pseudopterogorgia; (2) synthetic derivatives of pseudopterosin; and (3) the bicyclic derivatives or seco-analogs of the natural and synthetic pseudopterosin compounds of groups (1) and (2).

The generalized structure for pseudopterosin compounds belonging to groups (1) and (2) above is

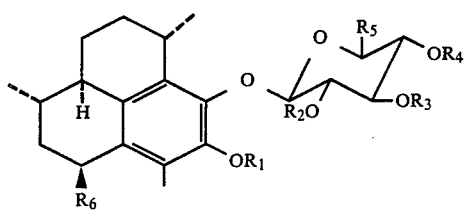

wherein $R_1$, $R_2$, $R_3$ and $R_4$ are hydrogen or an acyl residue (—COR) having from 1 to 6 carbon atoms, $R_5$ is hydrogen or $CH_2OH$ and $R_6$ is a hydrocarbon having from 1 to 10 carbon atoms.

Naturally occurring pseudopterosin compounds which have been isolated from Caribbean gorgonia are those where:
Compound I—$R_1$, $R_2$, $R_3$ and $R_4$=H; $R_5$=H; and $R_6$=2-methyl-1-propene-(pseudopterosin A)
Compound II—$R_1$, $R_2$, $R_4$=H; $R_3$=Acetate; $R_5$=H; and $R_6$=2-methyl-1-propene
Compound III—$R_1$, $R_3$, $R_4$=H; $R_2$=Acetate; $R_5$=H; and $R_6$=2-methyl-1-propene All of the above described pseudopterosin natural products can be isolated and purified by the same chemical methods. Freshly collected Pseudopterogorgia species are stripped of lateral branchlets and the combined branchlets are stored frozen. The defrosted animals are ground in warm 10% methanol in chloroform and the insoluble tissues are filtered. The filter cake is re-extracted twice with the same solvent. The extracts are combined and the solvents are removed by evaporation at reduced pressure and at a temperature under 40° C. The residual tar is dissolved in chloroform, dried by the addition of liberal quantities of anhydrous magnesium sulfate, the magnesium sulfate is filtered, and the solvent is once again removed at reduced pressure. The yield of residual "crude extract" is generally between 6 and 9% of the dry weight of the animal tissue.

The various naturally occurring pseudopterosin compounds are isolated from the "crude extract" by a series of sequential silica gel chromatographic techniques. Approximately 30 grams of extract is dissolved in isooctane and applied to a column (10×6 cm) of TLC-grade silica gel made in a sintered-glass vacuum funnel. The chromatography is conducted with solvent mixtures beginning with 100% isooctane and ending with 100% ethyl acetate. The process creates 12-15 "fractions" which contain various percentages of pseudopterosin derivatives. The final purification of the natural products is accomplished by high-performance liquid chromatography on 1.3×50 cm silica gel columns with appropriate isooctane-ethyl acetate mixtures.

In most cases pseudopterosins are isolated as viscous oils or amorphous solids, but in one case (Compound II), the derivative was crysalline. Additional details of isolation and purification of pseudopterosin and its naturally occurring derivatives are set forth in the published dissertation of S. A. Look which has been previously incorporated by reference.

The known naturally occurring pseudopterosin compounds are limited to those in which $R_6$ is 2-methyl-1-propene, $R_5$ is hydrogen and at least 3 of $R_1$, $R_2$, $R_3$ and $R_4$ are hydrogen and no more than one of $R_1$, $R_2$, $R_3$ or $R_4$ is acetate.

Synthetic derivatives of the naturally occurring pseudopterosin compounds include compounds according to the above general structure in which if $R_6$ is 2-methyl-1-propene, then $R_5$ is $CH_2OH$, or if $R_6$ is 2-methyl-1-propene and $R_5$ is hydrogen, then three or less of said $R_1$, $R_2$, $R_3$ or $R_4$ are hydrogen, and if one of $R_1$, $R_2$, $R_3$ or $R_4$ is acetate, then two or less of said $R_1$, $R_2$, $R_3$ or $R_4$ are hydrogen.

Exemplary groups which may be attached at the $R_1$, $R_2$, $R_3$ or $R_4$ position in addition to acetate are simple acyl derivatives having from 1 to 6 carbon atoms. Exemplary groups which may be attached at the $R_6$ position are alcohols, aldehydes, epoxides, ketones, acids, or other solubility-modifying groups as part of an alkyl residue from 4 to 10 carbon atoms.

Hydrogen is substituted at position $R_5$ when a pentose sugar moiety is desired with $R_5$ being $CH_2OH$ when a hexose moiety is desired.

Specific exemplary synthetic pseudopterosin compounds include:
Compound IV—$R_1$, $R_2$, $R_3$, $R_4$=Acetate; $R_5$=H; and $R_6$=2-methyl-1-propene.
Compound V—$R_1$, $R_2$, $R_3$, $R_4$=hydrogen; $R_5$=H; and $R_6$=2-methyl-1-propene-oxide;
Compound VI—$R_1$, $R_2$, $R_3$, $R_4$=hydrogen; $R_5$=H; and $R_6$=1-keto-2-methylpropane.
Compound VII—$R_1$, $R_2$, $R_3$, $R_4$=H; $R_5$=H; and $R_6$=2-methylpropane.

The procedures for substituting the wide variety of R groups into the pseudopterosin compound are conventional in nature and involve substitution of the $R_1$-$R_4$ group either on a ribose ($R_5$=hydrogen) or hexose ($R_5$=$CH_2OH$) ring structure or the $R_6$ group on the tricarbocyclic diterpene structure.

Exemplary synthesis of the selected synthetic derivatives is as follows:

Compound IV—Pseudopterosin (29 mg, 0.067 mM) was dissolved in 2 ml dry pyridine and excess acetic anhydride (ca. 1 ml) was added with stirring at room temperature. After 24 hours, 10 ml dichloromethane was added and the organic phase was subsequently washed with 1N hydrochloric acid, 5% sodium bicarbonate and saturated brine solutions. The organic phase was dried over anhydrous magnesium sulfate, and the solvent was removed under reduced pressure to yield the tetra-acetate derivative IV (32 mg, 79%) as a mobile oil. Successful acetylation and the full assignment of this derivative was accomplished by combined spectral techniques.

Compound V—Pseudopterosin (97 mg, 0.22 mm) was dissolved in 5 ml methylene chloride at room temperature. Metachloroperbenzoic acid (MCPBA) (49.2 mg, 0.26 mM), buffered with sodium biphosphate, was dissolved all at once, the solution was stirred for 22 hours, and next excess aq. sodium bisulfite was added. The organic phase was extracted first with saturated sodium bicarbonate solution, then with brine and finally dried over anhydrous magnesium sulfate. Removal of solvent after filtering left 97.2 mg (97%) of a viscous oil identified as the corresponding epoxide on the basis of complete structural analysis involving spectral methods.

Compound VI—Compound V (21.3 mg, 0.048 mM) in 3 ml anhydrous diethyl ether was treated with 0.2 ml boron trifluoride etherate (Aldrich Chem. Co.) at 0°. The solution was stirred for 20 min, 5 ml distilled water was added, and the organic phase was increased by the addition of an additional 5 ml ether. The ether layer was washed with 5% sodium bicarbonate, dried over anhydrous magnesium sulfate and reduced in vacuo. The crude product was purified by silica gel HPLC to yield the ketone derivative (13 mg, 61%) as a colorless viscous oil.

Compound VII—Pseudopterosin (58 mg, 0.13 mM) was combined with 5 ml ethyl acetate and a catalytic amount (ca. 20 mg) of 10% Palladium on carbon and the sealed flask was purged with hydrogen. The reaction was allowed to proceed for 72 hours and the catalyst was filtered. Removal of solvent at reduced pressure gave the dihydro product (32.7 mg, 56%) as a viscous oil which was sufficiently pure for further investigation on the basis of NMR analysis.

The bicyclic derivatives or seco analogs of the previously defined pseudopterosin compounds have the generalized structure:

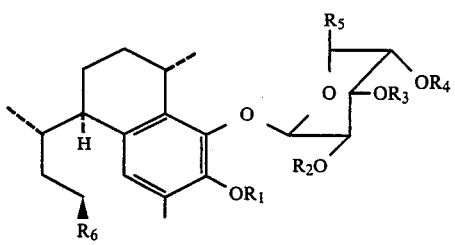

These derivatives or analogs are the same as the previous compounds except that they are the 1,12-seco analogs of the corresponding pseudopterosin compounds and they encompass alpha linked sugars. The various R groups listed in the formula have the same definition as the R groups for the pseudopterosin compound as previously discussed.

Exemplary natural seco analogs of pseudopterosin are:

Compound VIII—$R_1$, $R_2$, $R_3$=H; $R_4$=Acetate; $R_5$=H; and $R_6$=2-methyl-1-propene.

Compound IX—$R_1$, $R_2$, $R_3$, $R_4$=H; $R_5$=H; and $R_6$=2-methyl-1-propene.

Compound X—$R_1$, $R_2$, $R_4$=H; $R_3$=Acetate; $R_5$=H; and $R_6$=2-methyl-1-propene.

The above naturally occurring seco analogs of pseudopterosin are isolated from Caribbean gorgonians in the same manner as pseudopterosin. Details of an exemplary procedure are set forth in the dissertation of S. A. Look which has been previously referenced.

Preparation of 1,12-seco analog derivatives corresponding to the synthetic derivatives of pseudopterosin may be carried out by the same methods defined in detail for pseudopterosin.

The compounds of the present invention have been found to be effective anti-inflammatory agents, antiproliferative agents and analgesic agents for use in treating mammals. Examples demonstrating the effectiveness of selected representative exemplary compounds are set forth below.

Exemplary compounds I–X were tested according to the following well known pharmacological methods:

a. Mouse Ear Anti-Inflammatory Assay

Test compound and phorbol myristate acetate (PMA) are topically applied simultaneously to the pinnae of the ears of mice. Three hours twenty minutes after application, mice are sacrificed, ears removed and standard sized bores taken. Edema (inflammation) is measured as the difference in weight between control and treated ears.

b. Sperm Motility Assay

Male sea urchins are induced to spawn by injection of 0.5M KCl into the coelomic cavity. Sperm is collected via a pasteur pipette and stored in a test tube on ice. One drop of undiluted sperm is added to 25 ml of filtered fresh seawater, then 1.0 ml volumes of this solution are immediately added to test tubes containing 10 microliter test solution. Aliquots of sperm from each tube are observed microscopically for motility at a time two minutes after addition of sperm to test solution.

c. Fertilized Sea Urchin Egg Inhibition of Cleavage Assay for Anti-proliferation Sea urchins are induced to spawn by injection of 0.5M KCl into the coelomic cavity. Test compound is added to a 1% slurry of eggs within 5 minutes following fertilization and incubated until the completion of the division in control slurry, 90–120 minutes. Inhibition is measured as the percent of undivided cells in the slurry at the end of this incubation.

d. Phenylquinone Assay for Analgesia

Test compound is injected subcutaneously into mice. After 30 minutes, phenylquinone is injected intraperitoneally to cause pain as indicated by writhing. Absence of or a statistically significant decrease in writhing is considered evidence of analgesia [Hendershot, L. C. and G. Forsaith, Pharmacol. Exp. Ther. 125, 237 (1959)].

The results of the pharmacological testing are set forth in the following Tables I–VI.

TABLE I

Effect of Pseudopterosin (Compound I) on Phorbol Myristate Acetate (PMA) Induced Topical Inflammation of the Mouse Ear

| Treatment | Dose ug/ear | N | Ear Weight Mean ± S.E.M. |
|---|---|---|---|
| PMA alone | 1.5 | 24 | 20.83 ± 0.73 mg |
| PMA (1.5 ug) + Pseudopterosin A | 6.25 | 8 | 16.78 ± 0.91 mg** |
| | 12.5 | 24 | 14.99 ± 0.6 mg* |
| | 25.0 | 24 | 13.18 ± 0.53 mg* |
| | 50.0 | 24 | 12.47 ± 0.46 mg* |
| | 100.0 | 16 | 11.70 ± 0.37 mg* |

*Statistically signigicant difference, p < .01, Student's t-test
**Statistically signigicant difference, p < .05, Student's t-test

TABLE II

Effect of Pseudopterosin (Compound I) on Arachidonic Acid (A.A.) Induced Topical Inflammation of the Mouse Ear

| Treatment | Dose ug/ear | N | Ear Weight Mean ± S.E.M. |
|---|---|---|---|
| A.A. alone | 2500.0 | 8 | 16.37 ± 1.10 mg |
| A.A. (2500.0 ug) + Pseudopterosin A | 50.0 | 8 | 13.33 ± 0.38 mg** |

**Statistically significant difference, p < 0.05, Student's t-test

TABLE III

Analgesic Activity of Pseudopterosin (Compound I) Against Intraperitoneally Administered Phenylquinone (2.0 mg/kg)

| Treatment | Dose mg/kg | No. Animals | Mean No. Responses ± S.E.M. |
|---|---|---|---|
| Vehicle Control | — | 13 | 17.18 ± 0.90 |
| Pseudopterosin A | 3.1 | 9 | 8.55 ± 1.38* |
| Pseudopterosin A | 6.3 | 13 | 5.87 ± 1.24* |
| Pseudopterosin A | 12.5 | 13 | 5.87 ± 0.77* |
| Pseudopterosin A | 25.0 | 13 | 1.80 ± 1.31* |
| Pseudopterosin A | 50.0 | 5 | 0* |

*Statistically signigicant difference (p < 0.001) between control and each treated group. Student's t-test.

TABLE IV

Effects of Derivatives of Pseudopterosin on Phorbol Myristate Acetate Induced Topical Inflammation of the Mouse Ear

| Compound | Dose ug/ear | N | Mean Ear Weight ± S.E. |
|---|---|---|---|
| Pseudopterosin A Glycosides | | | |
| Acetone only | — | 16 | 11.25 ± 0.81 |
| PMA alone | 1.5 | 16 | 20.18 ± 4.29 |
| Compound II | 25.0 | 16 | 14.78 ± 2.79** |
|  | 50.0 | 16 | 14.31 ± 2.40** |
| Compound III | 25.0 | 16 | 15.28 ± 2.22* |
|  | 50.0 | 16 | 13.86 ± 2.16** |
| Compound V | 12.5 | 8 | 13.79 ± 2.14** |
|  | 25.0 | 8 | 13.75 ± 2.90** |
| Compound VI | 6.3 | 8 | 16.33 ± 3.87* |
|  | 12.5 | 8 | 15.39 ± 3.00* |
|  | 25.0 | 8 | 13.00 ± 1.50** |
| Compound VII | 6.3 | 8 | 18.00 ± 6.93 |
|  | 12.5 | 8 | 16.93 ± 4.47 |
|  | 25.0 | 8 | 11.82 ± 0.90** |
| Compound IV | 12.5 | 8 | 17.81 ± 3.78 |
|  | 25.0 | 8 | 14.42 ± 2.71** |
| Bicyclic Glycoside Derivatives of Pseudopterosin | | | |
| Compound VIII | 25.0 | 16 | 13.93 ± 2.59** |
|  | 50.0 | 16 | 12.07 ± 1.69** |
| Compound IX | 25.0 | 16 | 15.85 ± 2.51* |
|  | 50.0 | 16 | 14.04 ± 2.38** |
| Compound X | 50.0 | 6 | 10.64 ± 1.93** |

*Statistically significant, p < 0.05, Student's t-test, one-tailed
**Statistically significant, p < 0.01, Student's t-test, one-tailed

TABLE V

Analgesia Against Intraperitoneally Administered Phenylquinone

| Treatment | Dose mg/kg | No. Writhes | No. Animals | Mean Writhes per Animal | % Change Relative to Control |
|---|---|---|---|---|---|
| Vehicle | — | 83 | 9 | 9.2 | |
| Compound IX | 25 | 68 | 10 | 6.8 | −26 |
| Compound II | 25 | 91 | 10 | 9.1 | −1 |
| Compound IV | 25 | 55 | 9 | 6.1 | −34 |
| Vehicle | — | 103 | 9 | 11.4 | |
| Compound VII | 25 | 66 | 10 | 6.6 | −42 |
| Vehicle | — | 36 | 5 | 7.2 | |
| Compound XIII | 25 | 31 | 4 | 7.8 | +8 |
| Compound V | 25 | 22 | 5 | 4.4 | −39 |
| Vehicle | — | 47 | 4 | 11.8 | |
| Compound XI | 25 | 37 | 3 | 12.3 | +4 |
| Compound XII | 25 | 25 | 2 | 12.5 | +6 |

TABLE VI

Analgesic Activity of Compound III Against Intraperitoneally Administered Phenylquinone - Preliminary Dose Response Data

| Treatment | Dose mg/kg | N | Mean No. Writhes |
|---|---|---|---|
| Vehicle control | — | 4 | 8.63 ± 0.62 |
| Compound III | 6.3 | 3 | 5.11 ± 0.21* |
| Compound III | 12.5 | 3 | 3.98 ± 0.64* |
| Compound III | 25.0 | 3 | 1.20 ± 0.75* |

TABLE VI-continued

Analgesic Activity of Compound III Against Intraperitoneally Administered Phenylquinone - Preliminary Dose Response Data

| Treatment | Dose mg/kg | N | Mean No. Writhes |
|---|---|---|---|
| Compound III | 50.0 | 3 | 0 |

*Statistically significant difference, p < .05, Student's t-test

The vehicle or carrier for the compounds the assay was as follows: For the mouse ear inflammatory assay, the vehicle was acetone. Controls received 25 microliters of acetone. Test compounds were applied to the experimental animals in 25 microliter volumes. For the sperm motility and fertilized sea urchin egg assays, the compounds were dissolved in 10 microliters undenatured ethanol.

For the phenylquinone writhing assays, phenylquinone was administered at 2 mg per kg intraperitoneally in 5% ethanol-95% physiological saline. Test compound was administered subcutaneously in sesame oil at concentrations up to 5 mg per ml depending on the test compound dosage protocol. The highest dose was 50 mg per Kg. Control groups received sesame oil subcutaneously.

A summary of the results of the testing for anti-inflammatory and analgesic activity is set forth in Table VII.

TABLE VII

Summary of Anti-inflammatory and Analgesic Activities of Pseudopterosin A and its Derivatives

| Compound No. | Anti-inflammatory Activity | Analgesic Activity |
|---|---|---|
| Pseudopterosin A Glycosides | | |
| I | Active | Active |
| II | Active | Inactive |
| III | Active | Active |
| IV | Active | Active |
| V | Active | Active |
| VI | Active | Not Tested |
| VII | Active | Active |
| Bicyclic Glycoside Derivatives of Pseudopterosin | | |
| VIII | Active | Active |
| IX | Active | Active |
| X | Active | Not tested |

Application of 50 microgram pseudopterosin A (Compound I) results in a 69% decrease in edema. The standard anti-inflammatory agent indomethacin, by comparison, produces only a 50% decrease in edema at the same dose. Pseudopterosin also totally inhibits cell division at doses as low as $7 \times 10^{-6}$M, and sperm motility at the standard test dose of 16 microgram/ml ($10^{-5}$m). Pseudopterosin also provides analgesia against chemically induced pain. The other exemplary synthetic and natural derivatives of pseudopterosin which were tested provided similar results.

Pseudopterosin compounds in accordance with the present invention are a combination of a ribose, arabinose or hexose sugar moiety and a diterpene moiety. Exemplary diterpene or aglycone moieties were tested for analgesic and anti-inflammatory activity in the same manner as compounds I-X. The aglycones which were tested were:

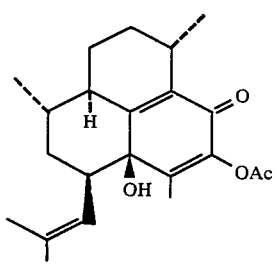

COMPOUND XI

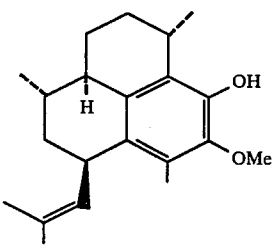

COMPOUND XII

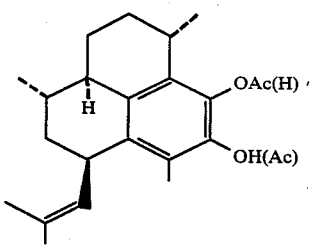

COMPOUND XIII

None of the three aglycones (XI–XIII) were found to have anti-inflammatory or analgesic activity. It is believed that the unique combination of the diterpene moiety and the sugar moiety in pseudopterosin and pseudopterosin derivative compounds is responsible for the biological activity of the compounds. The particular group ($R_1$–$R_6$) does not appear to be critical so long as the R groups are within those classes of hydrocarbon groups set forth in this specification. R groups having greater number of carbon atoms are preferred in many cases since they produce a compound having higher lipophilicity which provides improved membrane transport characteristics which are useful when the compounds are applied topically.

The following side effect of pseudopterosin A (Compound I) was observed. Doses of 12.5 mg/kg to 50 mg/kg, administered subcutaneously to mice (dissolved in sesame oil, 0.1 cc volume/10 gm body weight) produce central nervous system excitation, brief involuntary muscle contraction of the hind limbs resulting in lateral jumping movements, excessive preening of wound sites, and flushing of the tail and ears. These effects begin within a few minutes of administration and last up to one hour. Doses as low as 3 mg/kg produce slight to moderate central nervous system excitation.

Doses up to 50 mg/kg administered intraperitoneally to mice have no effect. At 100 mg/kg and above, pseudopterosin produces mild excitation and writhing in some animals, with return to normal activity within 30 minutes. Mortality at 100 mg/kg=2/10 on day after administration, at 200 mg/kg=2/4 also on day after administration.

The novel pseudopterosin compounds in accordance with the present invention are useful in the treatment of rheumatoid arthritis, osteoarthritis, rheumatic carditis, collagen and/or auto-immune diseases such as myasthenia gravis, allergic diseases, bronchial asthma and ocular and skin inflammatory diseases such as poison ivy. The compounds are also useful in treating poliferative diseases such as psoriasis.

The compounds are also useful as adjuvant therapy associated with organ and tissue transplants and any neurological disease involving metabolism of nervous tissue phospholipid such as multiple sclerosis. Because of their selective antagonism of chemical irritation (i.e., PMA inflammation) pseudopterosin compounds can be useful in the treatment of insect bites, bee or wasp stings or any venom in which a major constituent is the enzyme phospholipase $A_2$. The compounds are potent non-narcotic analgesics and may be used to alleviate pain resulting from traumatic injury or acute progressive disease, such as post operative pain, burns, or other conditions involving a coincident inflammation.

The pseudopterosin compounds in accordance with the present invention are administered to mammals including humans in an effective amount on the order of 10 to 50 mg per day per kilogram of body weight. The drug may be administered orally, parenterally, topically or by other standard administration routes. The dosage form may be by tablet containing normal acceptable additives, excipients, etc. The parenteral form contains typical aqueous intravenous solution ingredients such as propylene glycol and physiological saline or other suitable lipid solubilizing carrier.

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the specific embodiments as illustrated herein, but is only limited by the following claims.

What is claimed is:

1. A derivative of pseudopterosin having the structure:

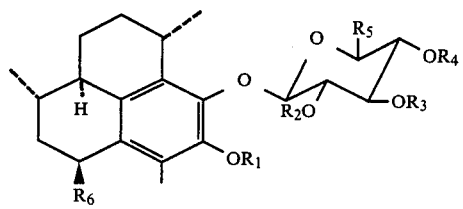

wherein $R_1$, $R_2$, $R_3$ and $R_4$ are hydrogen or an acyl residue having from 1 to 6 carbon atoms, $R_5$ is hydrogen or $CH_2OH$; $R_6$ is a hydrocarbon having from 1 to 10 carbon atoms; or an alkyl residue having from 4 to 10 carbon atoms; and wherein if $R_6$ is a 2-methyl-1-propene, then $R_5$ is $CH_2OH$ or if $R_6$ is a 2-methyl-1-propene and $R_5$ is hydrogen, then no more than three of said $R_1$, $R_2$, $R_3$, or $R_4$ are hydrogen and if one of $R_1$, $R_2$, $R_3$, or $R_4$ is acetate, then no more than two of said $R_1$, $R_2$, $R_3$, or $R_4$ are hydrogen and wherein $R_1$, $R_2$, $R_3$, and $R_4$ are not all acetate.

2. A derivative of pseudopterosin according to claim 1 wherein $R_5$ is hydrogen.

3. A derivative of pseudopterosin according to claim 1 wherein $R_6$ is 2-methyl-1propene oxide.

4. A derivative of pseudopterosin according to claim 3 wherein $R_6$ is 2-methyl-1propene oxide and $R_1$, $R_2$, $R_3$ and $R_4$ are hydrogen.

5. A derivative of pseudopterosin having the structure:

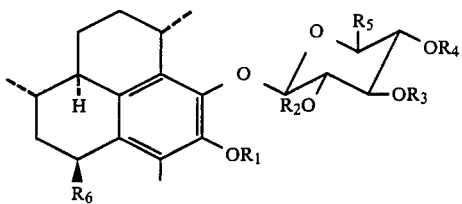

wherein $R_1$, $R_2$, $R_3$ and $R_4$ are hydrogen or an acyl residue having from 1 to 6 carbon atoms, $R_5$ is hydrogen or $CH_2OH$; and $R_6$ is 1-keto-2-methylpropane.

6. A derivative of pseudopterosin according to claim 5 wherein $R_1$, $R_2$, $R_3$ and $R_4$ are hydrogen.

7. A derivative of pseudopterosin having the structure:

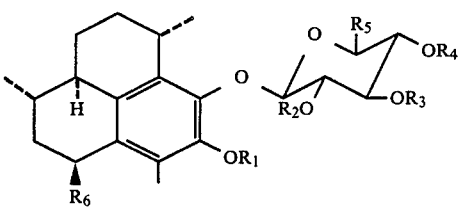

wherein $R_1$, $R_2$, $R_3$ and $R_4$ are hydrogen or an acyl residue having from 1 to 6 carbon atoms, $R_5$ is hydrogen or $CH_2OH$; and wherein $R_6$ is an alkyl group possessing between 4 and 10 carbon atoms.

8. A derivative of pseudopterosin according to claim 7 wherein $R_6$ is 2-methylpropane and $R_1$, $R_2$, $R_3$ and $R_4$ are hydrogen.

9. A derivative of pseudopterosin according to claim 4 wherein $R_5$ is hydrogen.

10. A derivative of pseudopterosin according to claim 6 wherein $R_5$ is hydrogen.

11. A derivative of pseudopterosin according to claim 8 wherein $R_5$ is hydrogen.

12. A derivative of pseudopterosin comprising the 1,12-seco analogs of compounds having the formula set forth in claim 1.

13. A composition for use as an anti-inflammatory agent in treating mammals, said composition consisting essentially of an effective amount of a pseudopterosin derivative according to claim 1 and a pharmaceutically acceptable carrier for said pseudopterosin derivative.

14. A composition for use as an analgesic agent in treating mammals, said composition consisting essentially of an effective amount of a pseudopterosin derivative according to claim 1 and a pharmaceutically acceptable carrier for said pseudopterosin derivative.

15. A method for treating mammals suffering from pain to reduce pain which comprises:
administering to said mammal a pain reducing effective amount of a composition consisting essentially of a compound having the structure:

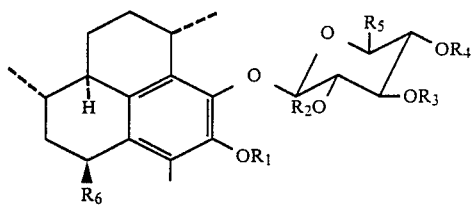

wherein $R_1$, $R_2$, $R_3$ and $R_4$ are hydrogen or an acyl residue (—COR) having from 1 to 6 carbon atoms, $R_5$ is hydrogen or $CH_2OH$ and $R_6$ is a hydrocarbon having from 1 to 10 carbon atoms; and a pharmaceutically acceptable carrier compound therefor.

16. A method for treating mammals having inflamed tissue to reduce inflammation which comprises:
administering to said mammal an inflammation reducing effective amount of a composition consisting essentially of a compound having the structure:

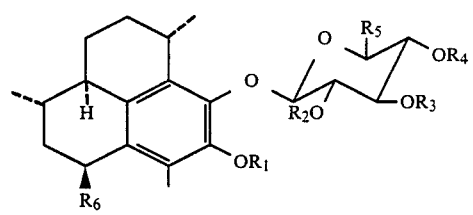

wherein $R_1$, $R_2$, $R_3$ and $R_4$ are hydrogen or an acyl residue having from 1 to 6 carbon atoms, $R_5$ is hydrogen or $CH_2OH$ and $R_6$ is a hydrocarbon having from 1 to 10 carbon atoms; and a pharmaceutically acceptable carrier compound therefor.

17. A method according to claim 15 wherein said compound is pseudopterosin.

18. A method according to claim 16 wherein said compound is pseudopterosin.

19. A method for treating mammals suffering from pain to reduce pain which comprises:
administering to said mammal a pain reducing effective amount of a composition consisting essentially of a pseudopterosin compound according to claim 1 and a pharmaceutically acceptable carrier compound therefor.

20. A method for treating mammals having inflamed tissue to reduce inflammation which comprises:
administering to said mammal an inflammation reducing effective amount of a composition consisting essentially of a pseudopterosin compound according to claim 1 and a pharmaceutically acceptable carrier compond therefor.

21. A method for treating mammals suffering from pain to reduce pain which comprises:
administering to said mammal a pain reducing effective amount of a composition consisting essentially of seco analogs of compounds having the structure:

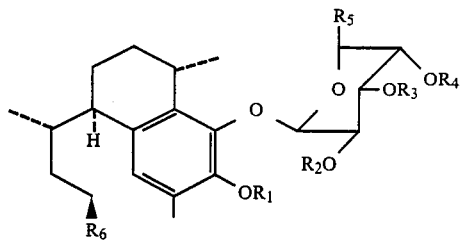

wherein $R_1$, $R_2$, $R_3$ and $R_4$ are hydrogen or an acyl residue having from 1 to 6 carbon atoms, $R_5$ is hydrogen or $CH_2OH$ and $R_6$ is a hydrocarbon having from 1 to 10 carbon atoms; and a pharmaceutically acceptable carrier compound therefor.

22. A method for treating mammals having inflamed tissue to reduce inflammation which comprises:
administering to said mammal an inflammation reducing effective amount of a composition consisting essentially of seco analogs of compounds having the structure:

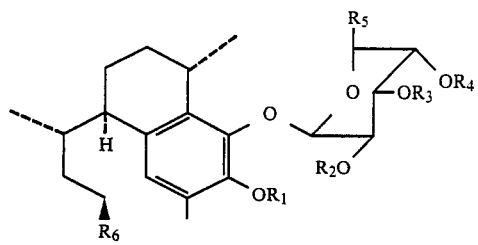

wherein $R_1$, $R_2$, $R_3$ and $R_4$ are hydrogen or an acyl residue having from 1 to 6 carbon atoms, $R_5$ is hydrogen or $CH_2OH$ and $R_6$ is a hydrocarbon having from 1 to 10 carbon atoms; and a pharmaceutically acceptable carrier compound therefor.

* * * * *